United States Patent

Tweden et al.

[19]

[11] Patent Number: 5,984,956
[45] Date of Patent: Nov. 16, 1999

[54] TRANSMYOCARDIAL IMPLANT

[75] Inventors: Katherine S. Tweden, Mahtomedi; Guy P. Vanney, Blaine; Thomas L. Odland, Lino Lakes, all of Minn.

[73] Assignee: HeartStent Corporation, St. Paul, Minn.

[21] Appl. No.: 08/944,313

[22] Filed: Oct. 6, 1997

[51] Int. Cl.[6] ........................................................ A61F 2/06
[52] U.S. Cl. ........................................ 623/1; 623/2; 623/12
[58] Field of Search ................................ 623/2, 1, 11, 12

[56] References Cited

U.S. PATENT DOCUMENTS

| | | | |
|---|---|---|---|
| 4,300,244 | 11/1981 | Bokros | 623/1 |
| 4,400,833 | 8/1983 | Kurland | 623/1 |
| 4,728,328 | 3/1988 | Hughes et al. | 623/1 |
| 4,769,029 | 9/1988 | Patel | 623/1 |
| 4,769,031 | 9/1988 | McGough et al. | 623/1 |
| 5,078,735 | 1/1992 | Mobin-Uddin | 623/1 |
| 5,222,980 | 6/1993 | Gealow | 623/26 |
| 5,254,113 | 10/1993 | Wilk | 623/12 |
| 5,429,144 | 7/1995 | Wilk . | |
| 5,443,497 | 8/1995 | Venbrux | 623/1 |
| 5,545,217 | 8/1996 | Offray et al. . | |
| 5,591,226 | 1/1997 | Trerotola et al. | 623/1 |
| 5,655,548 | 8/1997 | Nelson et al. . | |
| 5,755,682 | 5/1998 | Knudson et al. . | |

FOREIGN PATENT DOCUMENTS

| | | | |
|---|---|---|---|
| 84/02266 | 6/1984 | WIPO | 623/1 |
| 94/21197 | 9/1994 | WIPO | 623/1 |
| WO 97/27898 | 8/1997 | WIPO . | |
| WO 98/06356 | 2/1998 | WIPO . | |
| WO 98/08456 | 3/1998 | WIPO . | |

OTHER PUBLICATIONS

Sawyer, P. et al., "Electron microscopy and physical chemistry of healing in prosthetic heart valves, skirts, and struts", *The Journal of Thoracic and Cardiovascular Surgery*, vol. 67, No. 1, pp. 24–43 (Jan. 1974).

U.S. application No. 08/882,397, filed Jun. 25, 1997.

Schürmann, K. et al., "Iliac Arteries: Plain and Heparin–coated Dacron–covered Stent–Grafts Compared with Non–covered Metal Stents—An Experimental Study", *Radiology*, 203(1):55–63 (Apr. 1997).

*Primary Examiner*—Michael J. Milano
*Assistant Examiner*—Tram A. Nguyen
*Attorney, Agent, or Firm*—Merchant & Gould P.C.

[57] ABSTRACT

The transmyocardial implant for establishing blood flow through the myocardium between a heart chamber and a lumen of a coronary vasculature includes a hollow rigid conduit extending between the lumen and the heart chamber. The conduit is formed of a rigid material to resist deformation in response to contraction of the myocardium and the conduit is resistant to thrombus. A tissue growth-inducing material is secured to an exterior of the conduit. The tissue growth-inducing material is positioned to discourage tissue growth over openings of the implant.

24 Claims, 5 Drawing Sheets

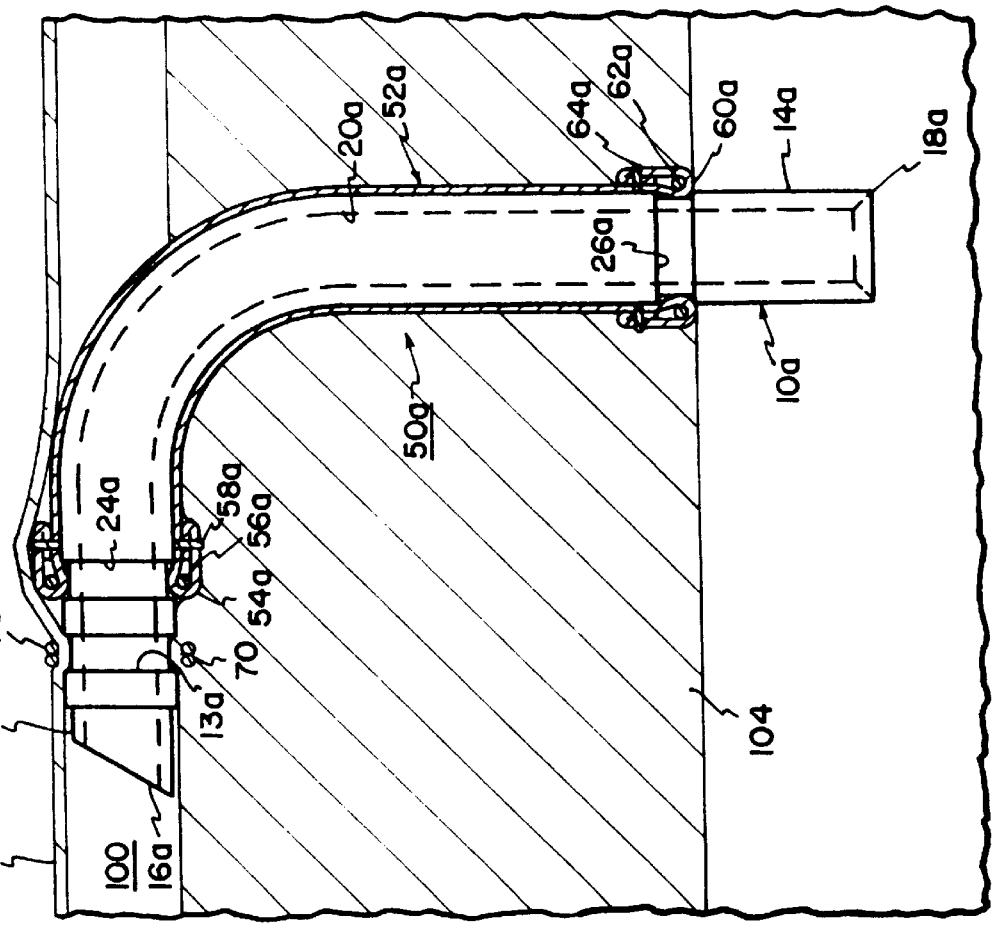
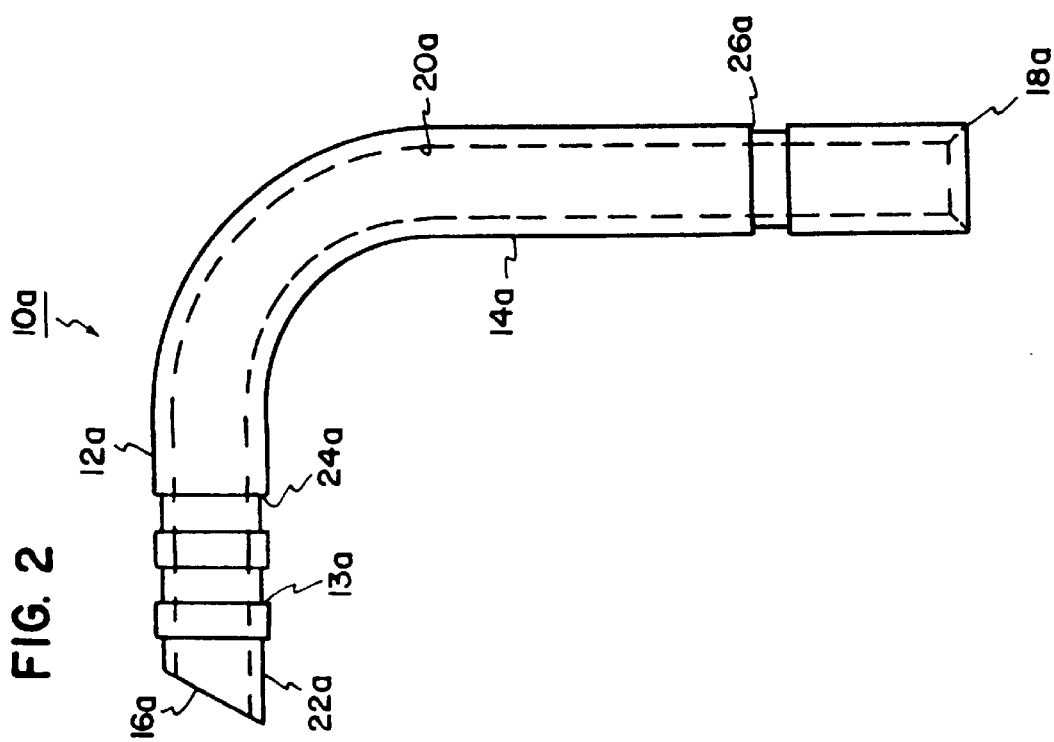

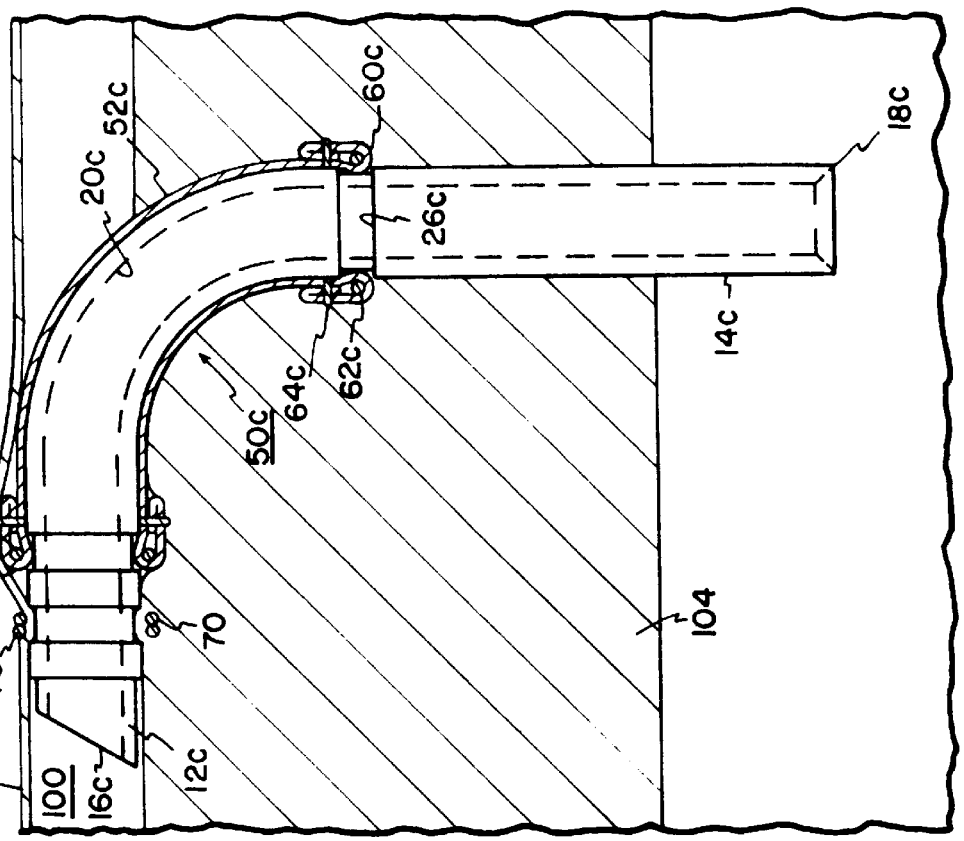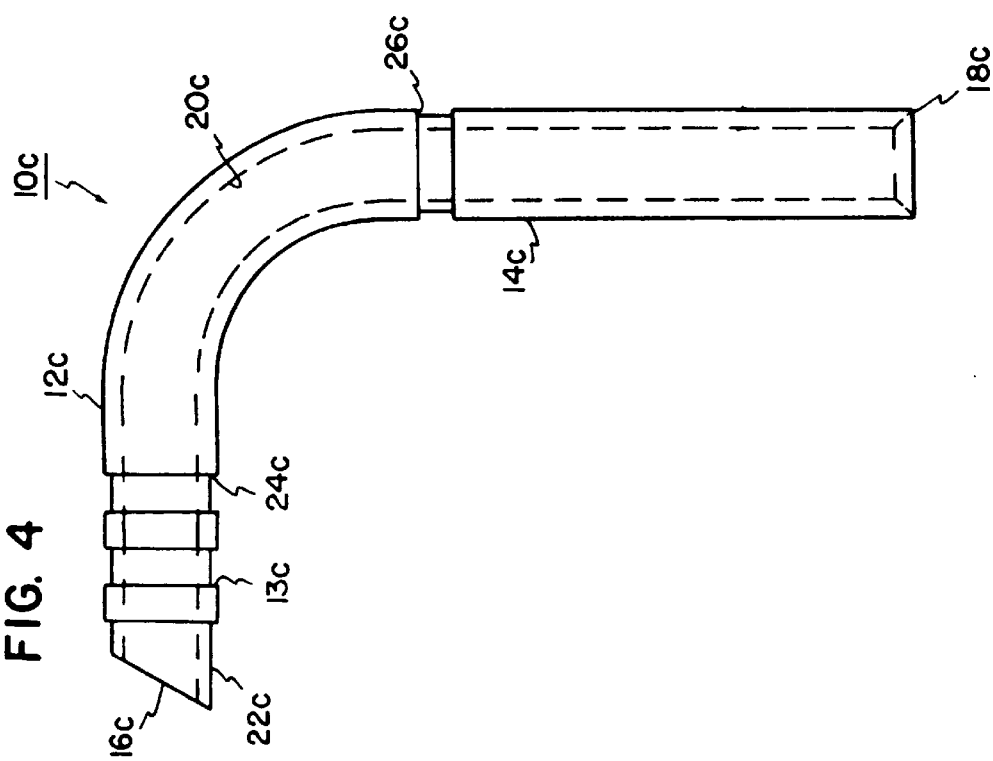

5,984,956

TRANSMYOCARDIAL IMPLANT

BACKGROUND OF THE INVENTION

1. Field of the Invention

This invention pertains to an implant for directing blood flow directly between a chamber of the heart and a coronary vasculature. More particularly, this invention pertains to such an implant with an enhanced design for securing placement of the implant.

2. Description of the Prior Art

U.S. patent application Ser. No. 08/882,397 filed Jun. 25, 1997, entitled "Method and Apparatus for Performing Coronary Bypass Surgery", and filed in the name of inventors Mark B. Knudson and William L. Giese, teaches an implant for defining a blood flow conduit directly from a chamber of the heart to a lumen of a coronary vasculature. An embodiment disclosed in the aforementioned application teaches an L-shaped implant in the form of a rigid conduit having one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

It is an object of the present invention to provide an improved transmyocardial implant with enhanced fixation structure.

SUMMARY OF THE INVENTION

According to a preferred embodiment of the present invention, a transmyocardial implant is disclosed for establishing a blood flow path through a myocardium between a heart chamber and a lumen of a coronary vasculature residing on an exterior surface of the myocardium. The implant includes a hollow rigid conduit with a first portion sized to be received within the lumen and with a second portion sized to extend from the vasculature through the myocardium and into the heart chamber. Open ends of the conduit define a blood flow pathway within an interior of the conduit between the heart chamber and the lumen of the vasculature. The conduit is formed of a material sufficiently rigid to resist deformation and closure of the pathway in response to contraction of the myocardium. Further, the conduit material is resistant to thrombus formation. A tissue growth-inducing material is secured to an exterior of the conduit.

BRIEF DESCRIPTION OF THE DRAWINGS

FIG. 2 is the view of FIG. 1 showing a first alternative embodiment of a conduit;

FIG. 2A is the view of FIG. 1A with the embodiment of FIG. 2 showing a tissue growth-inducing material in cross section;

FIG. 4 is the view of FIG. 1 showing a fourth embodiment of the conduit;

FIG. 4A is the view of FIG. 1A with the embodiment of the conduit of FIG. 4 and showing a tissue growth-inducing material in cross section;

DESCRIPTION OF THE PREFERRED EMBODIMENT

Figure 1A:
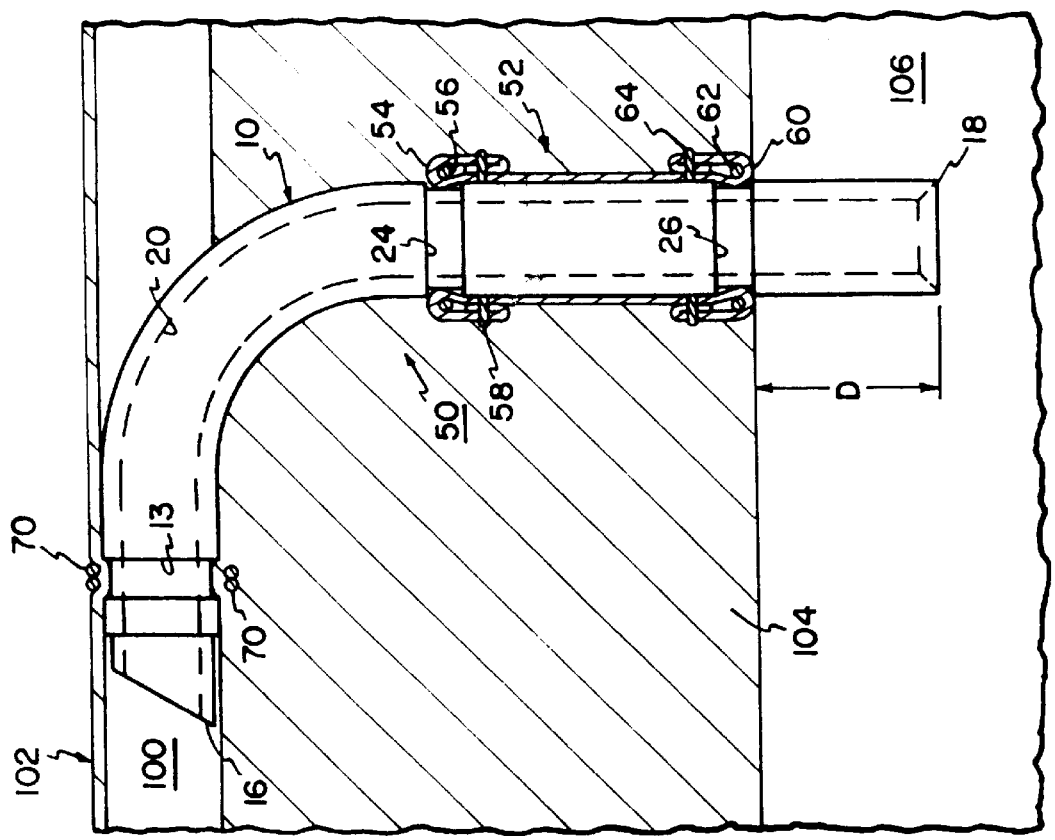
FIG. 1A is the view of FIG. 1 showing the implant of FIG. 1 and showing, in cross section, a tissue growth-inducing material secured to an exterior of the conduit and showing the implant positioned within the myocardium and lumen of a coronary vasculature.
Figure 1:
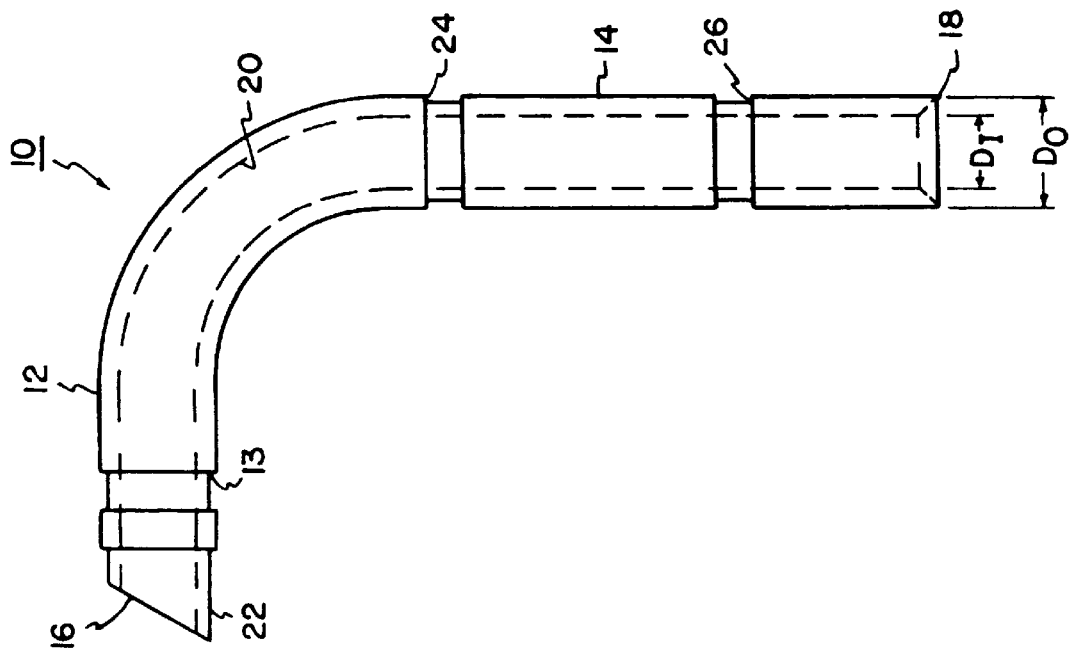
FIG. 1 is a side elevation view of an implant according to the present invention without showing a tissue growth-inducing material secured to an exterior of a conduit.

With initial reference to FIG. 1, a conduit 10 is shown in the form of an L-shaped rigid tube. The conduit 10 may be formed of titanium or other rigid biocompatible material such as pyrolytic carbon or may be titanium which is coated with pyrolytic carbon. The material of the conduit 10 is preferably a rigid material in order to withstand contraction forces of the myocardium, as will be described. In the preferred embodiment, the tube will have an outside diameter $D_O$ of about 3 millimeters and an internal diameter $D_I$ of about 2 millimeters to provide a wall thickness of about 0.5 millimeters.

The tube 10 has a first portion 12 which is sized to be received within the lumen of a coronary vasculature such as the lumen 100 of a coronary artery 102 illustrated in FIG. 1A. As used in this application, the term "vasculature" refers to veins or arteries. The conduit 10 has a second portion 14 which extends at a right angle to the axis of portion 12. The second portion 14 is sized to extend from the coronary artery 102 directly through the myocardium 104 and protrude into the left ventricle 106 of a patient's heart. The second portion 14 is sized to have a length sufficient for the portion 14 to protrude into the left ventricle 106.

The first portion 12 has a first opening 16 and the second portion 14 has a second opening 18 in communication with an interior 20 of the implant 10. Therefore, blood can freely flow through the implant 10 between the left ventricle 106 and the lumen 100 of the coronary artery 102. A leading end 22 of the first portion 12 is provided with a smaller external diameter and with a beveled face to permit ease of insertion of the leading end 22 into the coronary artery.

As mentioned, the tube 10 is preferably formed of titanium or other smooth biocompatible material in order to resist thrombus formation on the surfaces of the conduit 10. Titanium is a presently preferred material due to its long-term use in the cardiovascular industry. Further, titanium is sufficiently rigid to withstand deformation forces caused by contraction of the myocardium 104 to avoid deformation of the tube 10 so that the tube 10 remains open during both diastole and systole.

Figure 5:
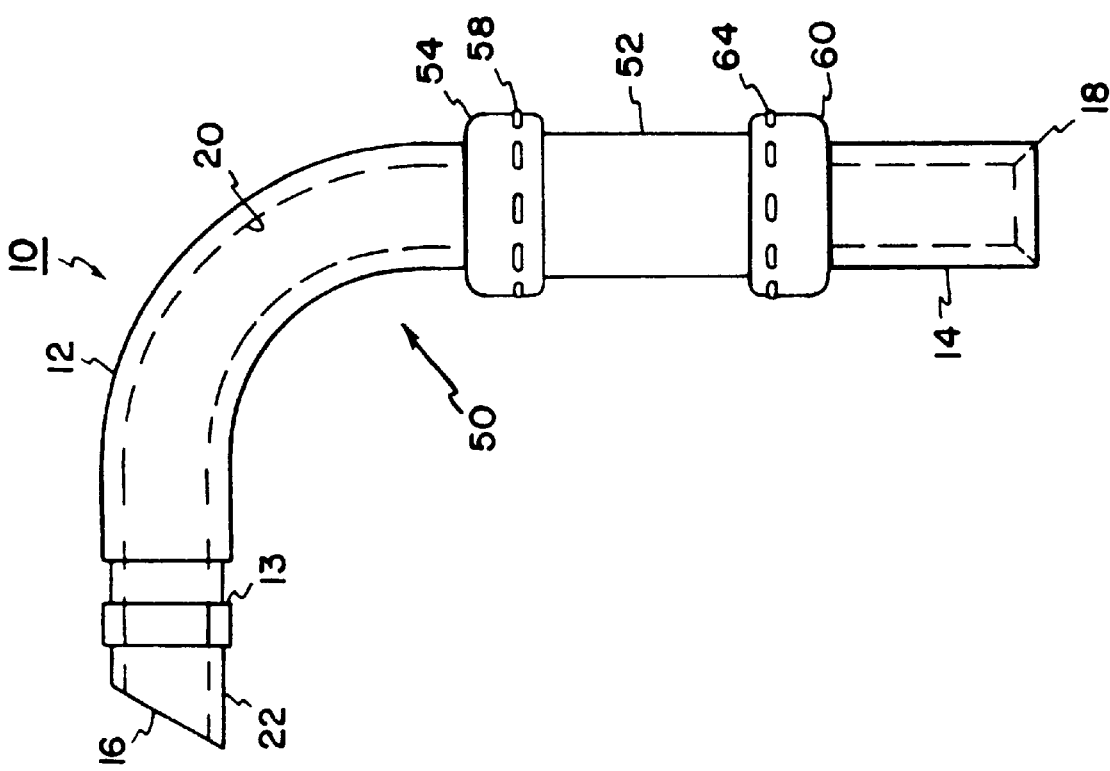
FIG. 5 is a side elevation view of the implant of FIG. 1A showing a tissue growth-inducing material secured to an exterior of the conduit of FIG. 1.

While tissue will adhere to titanium, the adhesion is inadequate when subjected to the shearing contracting forces of the myocardium due to the relative smoothness of extruded titanium. Therefore, a completed implant 50 is illustrated in FIGS. 1, 1A and 5 and includes a sleeve 52 of tissue growth-inducing material secured to an exterior surface of the conduit 10.

As illustrated in FIGS. 1 and 1A, the second portion 14 includes two spaced-apart reduced-diameter portions 24, 26 to define grooves in the second portion 14. The sleeve 52 includes a first end 54 with sutures 56 disposed around end 54 to retain end 54 within the groove 24. The material at the first end 54 is folded over the sutures 56 and stitched by stitching 58 to secure the first end 54 in the groove 24 and to immobilize the first end 54 relative to the tube 10. Similarly, a second end 60 of the sleeve 52 is retained by sutures 62 in the groove 26 and threading 64 secures the material of the sleeve 52 over the sutures 62. In the embodiments of FIGS. 1, 1A and 5, the sleeve 52 resides exclusively in the myocardium.

In the figures, the stitching 58,64 is shown exposed on an exterior of the sleeve 52. Alternatively, the sleeve 52 can be formed inverted so that the stitching 58,64 is not exposed.

Preferably, the sleeve 52 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric thereby anchoring the fabric and, hence, the tube 10 to the patient's tissue. Also, the enlarged portions resulting from folding the material of the sleeve over the sutures 62,56 enhances the volume of material susceptible to tissue integration, as well as providing a thickened area to further resist movement of the implant 50 relative to the myocardium 104. As a result, the sleeve 52 is selected to induce tissue attachment. Additionally, the first portion 12 is secured in place by means of a reduced-diameter groove 13 formed adjacent the leading end 22. With the reduced-diameter groove 13, a surgeon can place sutures 70 surrounding the coronary artery 102 to immobilize the coronary artery at the groove 13.

It is anticipated that tissue growth on and into the sleeve 52 could result in a buildup of tissue beyond the sleeve 52 to a thickness of about 1 millimeter. It is desirable that such tissue growth does not extend over ends 16, 18. Accordingly, the end 62 of the sleeve 52 is spaced from end 18 by a distance greater than an anticipated thickness of tissue growth extension beyond the sleeve 52. Since the anticipated thickness of tissue growth is about 1 millimeter, a minimum spacing of end 62 from tube end 18 of 1 millimeter is desired. However, a conservative additional spacing of 4–5 millimeters is preferred.

While a fabric tissue growth inducing material is illustrated, other materials could be used. For example, the tissue growth inducing material could be sintered metal on the external surface of the tube 10. Sintered metal results in a porous surface or layer to receive tissue growth. The area of the sintered metal will be spaced from ends 16, 18 to prevent tissue accumulation on the sintered area from growing over and blocking ends 16, 18.

FIGS. 2, 2A, 3, 3A, and 4, 4A show alternative embodiments of the present invention. In each of these embodiments, elements in common with those of FIGS. 1 and 1A are numbered identically and distinguished by letters "a", "b", and "c". Such elements will not be separately discussed with respect to the alternative embodiments except when necessary to distinguish between the embodiments.

In FIGS. 1 and 1A, the sleeve 52 resides exclusively in the myocardium 104. In the embodiment of FIGS. 2 and 2A, the groove 24a is moved to the intracoronary portion 12a such that the sleeve 52a resides in both the myocardium 104 and in the coronary artery 102 so that tissue growth can occur from the myocardium as well as the coronary artery 102 into the sleeve 52a. The embodiment of FIGS. 2 and 2A is a presently preferred embodiment to enhance fixation.

Figure 3A:
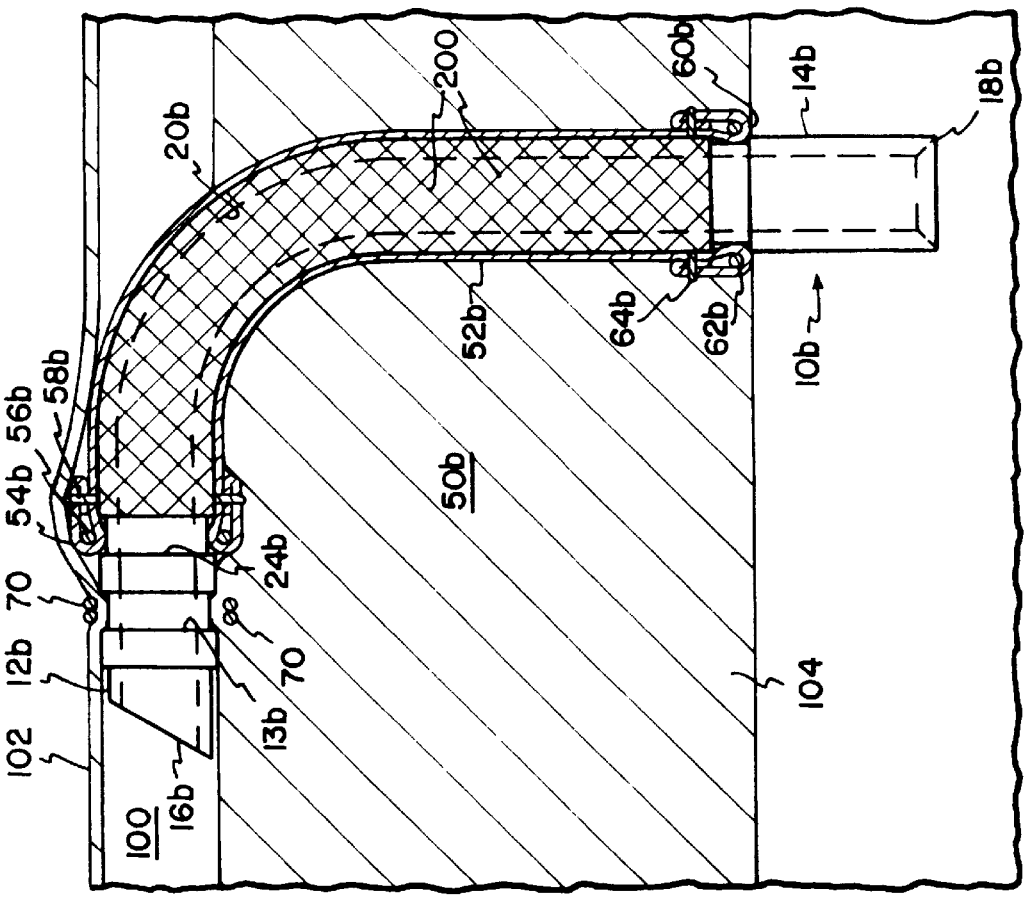
FIG. 3A is the view of FIG. 2A incorporating the conduit of FIG. 3.
Figure 3:
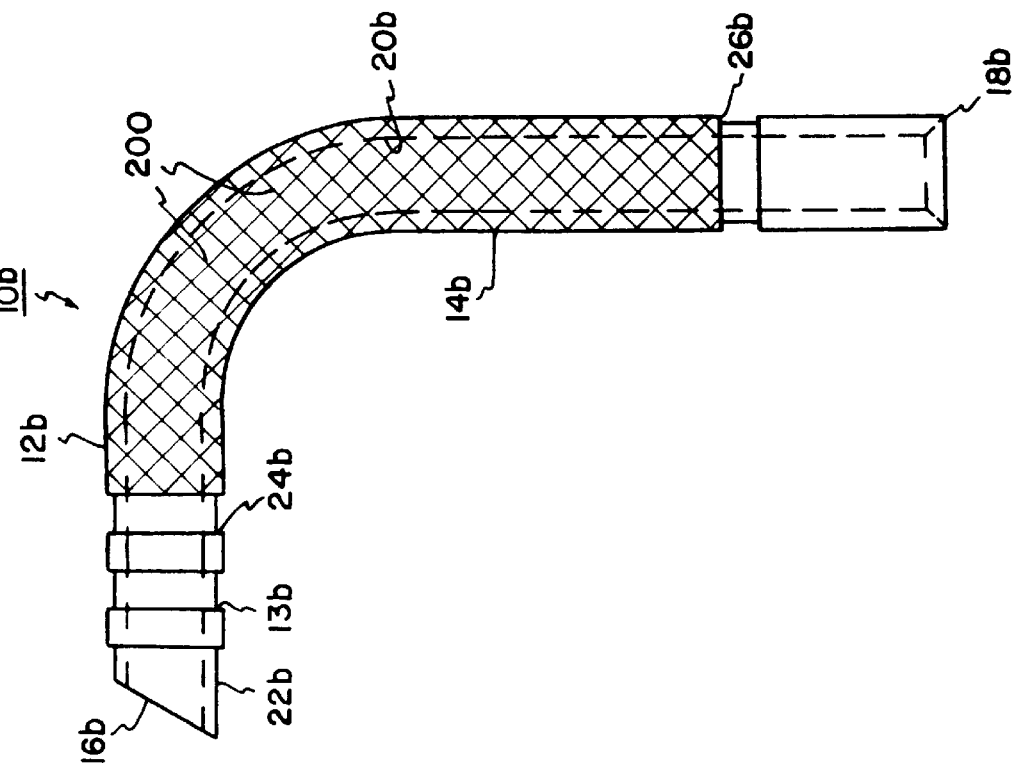
FIG. 3 is the view of FIG. 2 showing a modified external surface of a conduit.

In the embodiments of FIGS. 3 and 3A, the exterior surface of the tube 10b is roughened or abraded as indicated by hatch marks 200 in both the first portion 12b and second portion 14b. The roughening can be in the form of a knurling or a roughened surface due to sandblasting or the application of sinter beads. When the Dacron sleeve 52b is placed over the roughened surface 200, the sleeve 52b is restricted from motion relative to the exterior surface of the tube 10b due to enhanced friction resulting from the roughening 200. In addition, the roughening 200 provides a roughened surface with protrusions and pitting, around which tissue may grow as part of the tissue growth into the sleeve 52a.

FIGS. 4 and 4A are similar to the embodiments of FIGS. 2 and 2A except that the groove 26c has been moved from end 18c by a further distance so that the sleeve 52c resides primarily in the coronary artery 102 and only partially into the myocardium 104.

In all the embodiments, the tissue growth-inducing material of the sleeve 52c remains spaced from ends 16, 18 by a distance sufficient to avoid tissue growth on the material of the sleeve from extending over and blocking the ends 16, 18. As mentioned, an anticipated extension of tissue growth beyond sleeve 52 is about 1 millimeter so that the ends 54,60 should be spaced from tube ends 16, 18 by a minimum of 1 millimeter and preferably 4–5 millimeters to prevent tissue growth over ends 16, 18.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims which are appended hereto.

What is claimed:

1. A transmyocardial implant for establishing a blood flow path through a myocardium between a heart chamber and a lumen of a coronary vasculature residing at an exterior of said myocardium, said implant comprising:

a hollow rigid conduit having a first portion and a second portion, said first portion dimensioned so as to be received within said lumen and said second portion dimensioned so as to extend from said vasculature through said myocardium into said chamber, said conduit having open first and second ends on respective ones of said first and second portions to define a blood flow pathway within an interior of said conduit between said first and second ends;

said second portion having a solid wall construction with a smooth interior surface;

said second portion of said conduit formed of a conduit material sufficiently rigid to resist deformation and closure of said pathway in response to contraction of said myocardium and said conduit material resistant to thrombus formation;

a tissue growth inducing material secured to an exterior surface of said conduit at least partially surrounding said second portion; and said tissue growth inducing material is permanently spaced from at least one of said open first and second ends of said conduit by a distance to avoid tissue growth on said tissue growth inducing material from extending over and blocking said at least one of said open first and second ends of said conduit.

2. A transmyocardial implant according to claim 1 wherein said tissue growth inducing material is spaced from both of said open first and second ends of said conduit by a distance to avoid tissue growth on said tissue growth inducing material from extending over and blocking said open first and second ends of said conduit.

3. A transmyocardial implant according to claim 2 wherein said second portion is sized to extend into said chamber beyond said myocardium, said tissue growth inducing material is spaced from said second end.

4. A transmyocardial implant according to claim 1 wherein said tissue growth inducing material includes a plurality of fibers defining a plurality of interstitial spaces for receiving tissue growth and said tissue growth inducing material is biocompatible.

5. A transmyocardial implant according to claim 4 wherein said tissue growth inducing material is a polyester fabric.

6. A transmyocardial implant according to claim 1 wherein said tissue growth inducing material includes a porous layer on said exterior of said conduit.

7. A transmyocardial implant according to claim 1 wherein an external area of said conduit surrounded by said tissue growth inducing material is abraded.

8. A transmyocardial implant according to claim 1 wherein said tissue growth inducing material surrounds both said second portion and said first portion.

9. A transmyocardial implant for establishing a blood flow path through a myocardium between a heart chamber and a lumen of a coronary vasculature residing at an exterior of said myocardium, said implant comprising:

a hollow rigid conduit having a first portion and a second portion, said first portion dimensioned so as to be received within said lumen and said second portion dimensioned so as to extend from said vasculature through said myocardium into said chamber, said conduit having open first and second ends on respective ones of said first and second portions to define a blood flow pathway within an interior of said conduit between said first and second ends;

said second portion having a solid wall construction with a smooth interior surface;

said conduit formed of a conduit material sufficiently rigid to resist deformation and closure of said pathway in response to contraction of said myocardium and said conduit material resistant to thrombus formation;

a tissue growth inducing material secured to an exterior surface of said conduit at least partially surrounding said second portion; and wherein said tissue growth inducing material surrounds said second portion and not said first portion.

10. A transmyocardial implant according to claim 9 wherein said tissue growth inducing material is spaced from at least one of said open first and second ends of said conduit by a distance to avoid tissue growth on said tissue growth inducing material from extending over and blocking said at least one of said open first and second ends of said conduit.

11. A transmyocardial implant according to claim 10 wherein said second portion is sized to extend into said chamber beyond said myocardium, said tissue growth inducing material is spaced from said second end.

12. A transmyocardial implant according to claim 9 wherein said tissue growth inducing material includes a plurality of fibers defining a plurality of interstitial spaces for receiving tissue growth and said tissue growth inducing material is biocompatible.

13. A transmyocardial implant according to claim 12 wherein said tissue growth inducing material is a polyester fabric.

14. A transmyocardial implant according to claim 9 wherein said tissue growth inducing material includes a porous layer on said exterior of said conduit.

15. A transmyocardial implant according to claim 9 wherein an external area of said conduit surrounded by said tissue growth inducing material is abraded.

16. A transmyocardial implant for establishing a blood flow path through a myocardium between a heart chamber and a lumen of a coronary vasculature residing at an exterior of said myocardium, said implant comprising:

a hollow rigid conduit having a first portion and a second portion, said first portion dimensional so as to be received within said lumen and said second portion dimensioned so as to extend from said vasculature through said myocardium into said chamber, said conduit having open first and second ends on respective ones of said first and second portions to define a blood flow pathway within an interior of said conduit between said first and second ends;

said conduit formed of a conduit material sufficiently rigid to resist deformation and closure of said pathway in response to contraction of said myocardium and said conduit material resistant to thrombus formation;

said second portion having a solid wall construction with a smooth interior surface;

a tissue growth inducing material secured to an exterior surface of said conduit at least partially surrounding said second portion; and wherein said tissue growth inducing material surrounds said first portion and does not surround a complete length of said second portion.

17. A transmyocardial implant for establishing a blood flow path through a heart wall between a heart chamber and a lumen of a coronary vessel residing at an exterior of said wall, said implant comprising:

a conduit having a heart wall portion with an open chamber end, said conduit further having an open vessel end and an arcuate portion connecting said heart wall portion with said vessel end, said heart wall portion dimensioned so as to extend from said vessel through said heart wall into said chamber when said open vessel end is positioned within said lumen of said vessel, said conduit having a hollow interior defining a blood flow pathway between said heart chamber and vessel ends;

said heart wall portion having a solid wall construction with a smooth interior surface;

said heart wall portion of said conduit formed of a conduit material sufficiently rigid to resist deformation and closure of said pathway in response to contraction of said heart wall; and a tissue growth receiving material on an exterior surface of said conduit at least partially surrounding said heart wall portion.

18. A transmyocardial implant according to claim 17 wherein said tissue growth receiving material includes a plurality of fibers defining a plurality of interstitial spaces for receiving tissue growth and said tissue growth receiving material is biocompatible.

19. A transmyocardial implant according to claim 18 wherein said tissue growth receiving material is a polyester fabric.

20. A transmyocardial implant according to claim 17 wherein said tissue growth receiving material include a porous layer on said exterior surface of said conduit.

21. A transmyocardial implant according to claim 17 wherein an external area of said conduit is abraded.

22. A transmyocardial implant according to claim 17 wherein said tissue growth inducing material is spaced from said open chamber end by a distance to avoid tissue growth on said tissue growth receiving material from extending over and blocking said open chamber and vessel ends.

23. A transmyocardial implant according to claim 17 wherein said conduit is rigid throughout a length between said open chamber and vessel ends.

24. A transmyocardial implant according to claim 17 wherein said conduit material is titanium.

* * * * *

UNITED STATES PATENT AND TRADEMARK OFFICE
CERTIFICATE OF CORRECTION

PATENT NO. : 5,984,956
DATED : November 16, 1999
INVENTOR(S) : Tweden et al.

It is certified that error appears in the above-identified patent and that said Letters Patent is hereby corrected as shown below:

Column 6,
Line 9, "dimensional" should read -- dimensioned --

Column 7,
Line 2, "include" should read -- includes --

Signed and Sealed this

Fourteenth Day of May, 2002

Attest:

JAMES E. ROGAN
Attesting Officer   Director of the United States Patent and Trademark Office